United States Patent [19]

Bacon et al.

[11] Patent Number: 5,346,688
[45] Date of Patent: Sep. 13, 1994

[54] IODINATED WETTING AGENTS

[75] Inventors: Edward R. Bacon, East Greenbush, N.Y.; Gregory L. McIntire, West Chester, Pa.

[73] Assignee: Sterling Winthrop Inc., New York, N.Y.

[21] Appl. No.: 991,640

[22] Filed: Dec. 16, 1992

[51] Int. Cl.$^5$ .............................................. A61K 49/04
[52] U.S. Cl. ............................................. 424/5; 560/47
[58] Field of Search ........................... 560/25, 47, 77; 514/533; 424/5

[56] References Cited

U.S. PATENT DOCUMENTS 3,144,479  8/1964  Obendorf .

FOREIGN PATENT DOCUMENTS 1082368  5/1960  Fed. Rep. of Germany .
866184  4/1958  United Kingdom .

OTHER PUBLICATIONS

Chemical Abstract 57: 4604a Search Report (STN); 1962.

*Primary Examiner*—José G. Dees
*Assistant Examiner*—Samuel Barts
*Attorney, Agent, or Firm*—William J. Davis

[57] ABSTRACT

Compounds having the structure $$(Z)\!\!-\!\!COO\!\!-\!\!L\!\!-\!\!CO_2M$$

wherein (Z)—COO is the residue of an iodinated aromatic acid;

M is H, a cation, $-(CH_2CH_2O)_m H$, and $-(CH_2CH(OH)O)_p H$;

m is an integer from 1 to 150;

p is an integer from 1 to 50; and

L is one or more divalent linking groups selected from alkylene, cycloalkylene, arylene, arylenealkylene, and alkylenearylene are particularly useful as wetting agents in x-ray imaging compositions.

5 Claims, No Drawings

IODINATED WETTING AGENTS

FIELD OF THE INVENTION

This invention relates to iodinated aromatic compounds which are particularly useful as wetting agents.

BACKGROUND OF THE INVENTION

X-ray imaging is a well known and extremely valuable tool for the early detection and diagnosis of various disease states in the human body. The use of contrast agents for image enhancement in medical x-ray imaging procedures is widespread. An excellent background on iodinated and other contrast agents for medical imaging is provided by D. P. Swanson et al, Pharmaceuticals in Medical Imaging, 1990, MacMillan Publishing Company.

EP-A 498,482 describes nanoparticulate x-ray contrast compositions which have proven to be extremely useful in medical imaging. The particles consist of a poorly soluble diagnostic agent having adsorbed thereon a non-crosslinked surface modifier, the particles having a mean particle size of less than about 400 (nm).

The present invention is directed to novel iodinated surfactants which are particularly useful as surface modifiers in nanoparticle formulations.

SUMMARY OF THE INVENTION

We have discovered and prepared novel iodinated aromatic compounds which are particularly useful as wetting agents in x-ray contrast compositions.

More specifically, in accordance with this invention, there are provided novel compounds having the structure

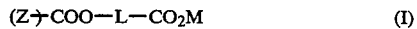

$$(Z)\text{-COO-L-CO}_2M \qquad (I)$$

wherein (Z)—COO is the residue of an iodinated aromatic acid;

M is H, a cation $(\text{CH}_2\text{CH}_2\text{O})_m\text{H}$, or $(\text{CH}_2\text{CH(OH)O})_p\text{H}$;

m is an integer from 1 to 150;

p is an integer from 1 to 50; and

L is one or more divalent linking groups selected from alkylene, cycloalkylene, arylene, arylenealkylene, and alkylenearylene.

It is an advantageous feature of this invention that iodinated wetting agents are provided for x-ray contrast compositions which agents contribute to contrast enhancement It is another advantageous feature that the wetting agents of this invention can be used in vivo to change the interaction of particles with the reticuloendothelial system, thus enabling the particles to be retained in the blood pool or targeted to specific organs.

Still another advantageous feature is that the use of the wetting agents of this invention can result in very small particles, e.g., less than about 100 nm in size, exhibiting both unique biological distribution, i.e., passive tumor targeting, and enhanced pharmaceutical stability.

DESCRIPTION OF PREFERRED EMBODIMENTS

The compounds of this invention are described herein primarily in connection with their preferred utility, i.e., as wetting agents for particulate x-ray contrast agents. However, the compounds are also expected to be useful as wetting agents for therapeutic agents and in various other applications.

In structural formula I above, (Z)—COO is the residue of an iodinated aromatic acid. The iodinated aromatic acid can comprise one, two, three or more iodine atoms per molecule. Preferred species contain at least two, and more preferably, at least three iodine atoms per molecule. The iodinated compounds can contain substituents which do not deleteriously effect the contrast enhancing capability of the compound.

Illustrative examples of suitable aromatic acids include diatrizoic acid,
metrizoic acid,
urokonic acid,
iothalamic acid,
trimesic acid,
ioxaglic acid (hexabrix),
ioxitalamic acid,
tetraiodoterephthalic acid,
iodipamide, and the like.

In preferred embodiments, (Z)—COO is the residue of a substituted triiodobenzoic acid such as an acyl, carbamyl, and/or acylamino substituted triiodobenzoic acid.

In a particularly preferred embodiment, Z represents

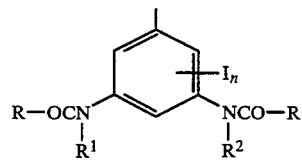

wherein n=1, 2 or 3, each R independently is H, $C_1$-$C_{18}$ alkyl, or $C_1$-$C_{18}$ fluoroalkyl, and $R^1$ and $R^2$ are independently H or $C_1$-$C_{18}$ alkyl.

M is H; a cation, such as an alkaline or alkaline earth cation such as $Na^+$, $K^+$, $Li^+$, $Ca^{++}$, $Ba^{++}$, or an ammonium cation such as $NH_4^+$, tetramethylammonium, and the like; $(\text{CH}_2\text{CH}_2\text{O})_m\text{H}$, or $(\text{CH}_2\text{CH(OH)O})_p\text{H}$; wherein m=an integer from 1 to 150, and p=an integer from 1 to 50.

L represents a divalent linking group preferably selected from alkylene containing from 1 to 20, preferably 1 to 8 carbon atoms such as methylene, ethylene, propylene, butylene, pentylene, hexylene, heptylene and the like; cycloalkylene, preferably containing from 3 to 12 carbon atoms such as cyclopropylene, cyclobutylene, cyclopentylene, cyclohexylene and the like; arylene, preferably containing from 6 to 10 carbon atoms such as phenylene and naphthylene; arylenealkylene, the alkylene and arylene portions of which are as described above; and alkylenearylene, the alkylene and arylene portions of which are as describe above.

The alkylene, cycloalkylene, arylene, alkylenearylene and arylenealkylene groups in Structure I above can be unsubstituted or substituted with various substituents which do not adversely affect the stability or efficacy of the compounds. Suitable substituents include alkyl, fluoroalkyl, cycloalkyl, aryl, aralkyl, alkoxy, hydroxy, aryloxy, acyloxy, halogen, acylamino, carboalkoxy, carbamyl and the like. However, reactive substituents are not preferred on the carbon atom adjacent to the ester group.

The compounds of this invention can be prepared by reacting the carboxylate of an iodinated aromatic acid with a functionalized acid having the formula X—L—CO$_2$M wherein X is a leaving group and L and M are as defined above, in a suitable solvent. Suitable leaving groups include halogen, such as Br, I, and Cl sulfonyloxy, such as methanesulfonyloxy and toluenesulfonyloxy. The carboxylates of iodinated aromatic acids and functionalized acids useful as the starting materials in the preparation of the compounds of this invention are known compounds and/or can be prepared by techniques known in the art. For example, suitable acids include commercially available bromoacids and chloroacids. A general reaction scheme is as follows:

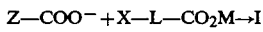

The reaction can take place at various temperatures ranging between −78° C. and 100° C., and preferably −40° C. to 50° C.

For convenience, the reaction can take place at ambient pressure, however, higher and lower pressures are contemplated.

Alternatively, the compounds of this invention, when M=H or a cation, can be prepared in a two-step synthesis. First, the carboxylate of an iodinated aromatic acid can be reacted with a functionalized ester as described by Bacon et al in commonly owned U.S. Pat. application Ser. No. 07/990,987, entitled Iodinated Aroyloxy Esters, filed on Dec. 16, 1992, or by Singh et al in commonly owned U.S. Pat. application Ser. No. 07/990,306, entitled Iodinated Aromatic Compounds, filed on Dec. 14, 1992, the disclosures of which are hereby incorporated by reference in their entirety. Thereafter, the ester can be converted into the corresponding acid by hydrolysis using techniques well known in the art.

The following are specific specific illustrative examples of preferred compounds of this invention that have been prepared:

5-[(3',5'-bis(acetylamino)-2',4',6'-triiodophenyl)carbonyloxy]pentanoic acid (WIN 68040),
6-[(3',5'-bis(acetylamino)-2',4',6'-triiodophenyl)carbonyloxy]hexanoic acid (WIN 68056),
7-[(3',5'-bis(acetylamino) -2',4',6'-triiodophenyl)carbonyloxy]heptanoic acid (WIN 68167),
8-[(3',5'-bis(acetylamino)-2',4',6'-triiodophenyl)carbonyloxy]octanoic acid (WIN 68237), and
4-[(3',5'-bis(acetylamino)-2',4',6'-triiodophenyl)carbonyloxymethyl]benzoic acid (WIN 68016) .

Preferred compounds of this invention having Structure I above, wherein Z is the residue of diatrizoic acid and M=H, are set forth below:

| WIN | L |
|---|---|
| 68040 | (CH$_2$)$_4$ |
| 68056 | (CH$_2$)$_5$ |
| 68167 | (CH$_2$)$_6$ |
| 68273 | (CH$_2$)$_7$ |
| 68016 | —CH$_2$—C$_6$H$_4$- |

When used as a wetting agent in an x-ray contrast composition, the compound of this invention can comprise up to about 40% or higher iodine by weight.

In preferred embodiments, the compounds of this invention can be formulated as wetting agents into particulate x-ray contrast compositions, preferably as surface modifiers in nanoparticulate x-ray contrast compositions, as described in commonly-owned EPO 498,482, the disclosure of which is hereby incorporated by reference in its entirety. Such nanoparticulate compositions can be prepared by dispersing a poorly soluble x-ray contrast agent in a liquid dispersion medium, and wet grinding the agent in the presence of rigid grinding media and a wetting agent of this invention to form the nanoparticles. Alternatively, the wetting agent can be contacted with the contrast agent after attrition.

The relative amount of the particulate x-ray contrast agent and wetting agent can vary widely and the optimal amount of the wetting agent can depend, for example, upon the particular contrast agent and wetting agent selected, the hydrophilic lipophilic balance of the wetting agent, its water solubility, the surface tension of water solutions of the wetting agent, etc. The wetting agent can be present in an amount of 0.1–90%, preferably 1–75%, more preferably 2–50% and most preferably 2–25% by weight based on the total combined dry weight of the particulate contrast agent and wetting agent.

The x-ray contrast compositions of this invention comprise the above-described compounds, preferably as a wetting agent for a particulate contrast agent, and a physiologically acceptable carrier therefor. For example, the particles can be dispersed in an aqueous liquid which serves as the carrier for the x-ray contrast agent. Other suitable carriers include liquid carriers such as mixed aqueous and nonaqueous solvents, such as alcohol; gels; gases, such as air; and powders.

The x-ray contrast composition can comprise from about 1–99.9, preferably 2–45 and more preferably 10–25% by weight of the above-described particles, the remainder of the composition being the carrier, additives and the like. Compositions up to about 100% by weight of the particles are contemplated when the composition is in a lyophilized form.

The dose of the contrast agent to be administered can be selected according to techniques known to those skilled in the art such that a sufficient contrast enhancing effect is obtained. Typical doses can range from 50 to 350 mg of iodine per kilogram of body weight of the subject for many imaging applications. For some applications, e.g., lymphography, lower doses, e.g., 0.5–20 mg I/kg, can be effective.

The x-ray contrast composition can contain one or more conventional additives used to control and/or enhance the properties of the x-ray contrast agent. For example, thickening agents such as dextran or human serum albumin, buffers, viscosity regulating agents, suspending agents, peptizing agents, anti-clotting agents, mixing agents, and other drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

A method for diagnostic imaging for use in medical procedures in accordance with this invention comprises administering to the body of a test subject in need of an x-ray an effective contrast producing amount of the above-described x-ray contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to x-rays to produce an x-ray image pattern corresponding to the presence of the contrast agent. The image pattern can then be visualized. For example, any x-ray visualization technique, preferably, a high contrast technique such as computed tomography, can be applied in a conventional manner. Alternatively, the image pattern can be observed directly on an x-ray sensitive phosphor screen-silver halide photographic film combination.

The compositions of this invention can be administered by a variety of routes depending on the type of procedure and the anatomical orientation of this tissue being examined. Suitable administration routes include intravascular (arterial or venous) administration by catheter, intravenous injection, rectal administration, subcutaneous administration, intramuscular administration, intralesional administration, intrathecal administration, intracisternal administration, oral administration, administration via inhalation, administration directly into a body cavity, e.g., arthrography, and the like.

In addition to preferred applications, i.e., for blood pool, liver, spleen and lymph node imaging, the x-ray contrast compositions of this invention are also expected to be useful as contrast agents for any organ or body cavity. For example, the compositions of this invention are expected to be useful as anglographic contrast media, urographic contrast media, myelographic contrast media, gastrointestinal contrast media, cholecystographic and cholangiographic contrast media, arthrographic contrast media, hysterosalpingographic contrast media, oral contrast media and bronchographic contrast media.

The following examples further illustrate the invention.

EXAMPLE 1

Preparation of WIN 68016

A mixture of WIN 67923, i.e., 4-(ethoxycarbonyl)-phenyl3, 5-bis(acetylamino) 2,4,6-triiodobenzoate, (11.8 g, 15.2 mmol) prepared by reacting sodium diatrizoate and ethyl 4-bromomethylbenzoate, as described by Singh et al, cited above, and sodium hydroxide (0.8 g, 20.0 mmol) in 100 ml of water and 50 ml of methanol was stirred and heated under reflux for 5 hrs. The methanol was removed under reduced pressure and the remaining solution was filtered to remove some insoluble solids. The filtrate was acidified with concentrated HCl whereupon a white solid precipitated. The precipitate was collected, washed with water and dried under vacuum at 80°-85° C. to give 9.8 g of a white granular solid, mp 289°-292° C. (dec.); CI-MS: MH+749. The $^1$H-NMR (300 MH$_z$) spectral data was consistent with the desired product. Calculated for $C_{19}H_{15}I_3N_2O_6$: C 30.51, H 2.02, I 50.89, N 3.74; Found: C 30.35, H 1.91, I 51.05, N 3.62.

EXAMPLE 2

Preparation of WIN 68056

A mixture of the ester, WIN 67722, i.e., 6-ethoxy-6-oxohexyl-3,5-bis(acetamide)2,4,6-triiodobenzoate, prepared as described by Bacon et al, cited above, (5.6 g, 7.3 mmol) and powdered 95% potassium hydroxide (1.6 g, 24.1 mmol) in 25 ml of water was heated on a steam bath for 15 minutes. After cooling, the resulting solution was filtered and acidified with glacial acetic acid. The precipitate that formed was collected, washed with a solution (1:1) of ethanol-ethyl ether and dried to give the crude product (93%). Recrystallization from DMF gave analytically pure material, mp 251°-255° C.; CI-MS: MH+ 729. The $^1$H-NMR (300 MHz) spectral date was consistent with the desired material. Calculated for $C_{17}H_{19}I_3N_2O_6$: C 28.05, H 2.63, I 52.29, N 3.85; Found: C 28.05, H 2.63, I 52.39, N 3.78.

EXAMPLE 3

Wetting Agent for X-Ray Nanoparticle

WIN 68056 was mixed at concentrations of 0.5 to 3% with WIN 67722 together with water sufficient to prepare a 10% suspension of WIN 67722. After milling for 7 days, the particle size was reduced to approximately 110 to 130 nm, as determined by standard light scattering techniques.

EXAMPLE 4

Wetting Agent for X-Ray Nanoparticle

WIN 68016 was treated as described above together with WIN 67722 and resulted in particles with an average size of less than 110 nm as determined by standard light scattering techniques.

The foregoing specification, including the specific embodiments and examples is intended to be illustrative of the present invention and is not to be taken as limiting. Numerous other variations and modifications can be effected without departing from the true spirit and scope of the present invention.

We claim:

1. A compound having the structure

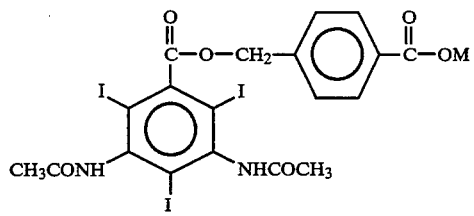

wherein M is H or a cation.

2. A compound having the structure

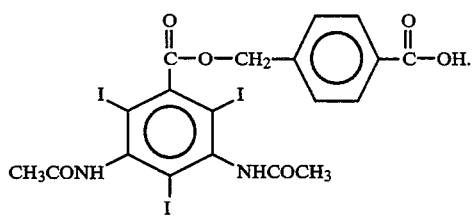

3. An x-ray contrast composition comprising the compound of claim 1.

4. The x-ray contrast composition of claim 3 further including a pharmaceutically acceptable carrier.

5. A method of medical x-ray diagnostic imaging which comprises administering to the body of a mammal a contrast effective amount of the x-ray contrast composition of claim 3.

* * * * *